United States Patent [19]

Radowitz

[11] 4,216,205

[45] Aug. 5, 1980

[54] PROCESS OF PREPARING A SERUM PROTEIN COMPOSITION FOR INTRAVENOUS APPLICATION

[75] Inventor: Markus Radowitz, Krefeld, Fed. Rep. of Germany

[73] Assignee: Armour Pharmaceutical, Scottsdale, Ariz.

[21] Appl. No.: 871,620

[22] Filed: Jan. 23, 1978

[30] Foreign Application Priority Data

Jan. 26, 1977 [CH] Switzerland ............................ 934/77
Mar. 17, 1977 [AT] Austria ................................. 1859/77

[51] Int. Cl.$^2$ ........................ A61K 35/14; C07G 7/00
[52] U.S. Cl. .................................. 424/101; 260/112 B
[58] Field of Search ...................... 424/101; 260/112 B

[56] References Cited

U.S. PATENT DOCUMENTS

| | | | |
|---|---|---|---|
| 3,770,631 | 11/1973 | Fekete et al. | 424/101 |
| 3,850,903 | 11/1974 | Garcia et al. | 424/101 |
| 4,073,886 | 2/1978 | Kehm | 424/101 |

*Primary Examiner*—Delbert R. Phillips
*Attorney, Agent, or Firm*—Cushman, Darby & Cushman

[57] ABSTRACT

A process of preparing a serum protein composition for intravenous application or administration, in which process, starting from a human blood protein solution, a stabilized, universally applicable preparation or composition is prepared which contains dissolved in an aqueous isotonic solution, such proteins in which the ratio of globulins and albumins corresponds substantially to that of the native blood serum, in the following steps:

(a) fractionation of human blood plasma upon removal of coagulation factors according to a process known per se recovering thereby precipitates and supernatants of different fractionation steps, (b) mixing and resolving of precipitates of different fractionation steps, preferably the COHN-fractions IV, III-1 and III-2), in which blood proteins, especially albumin and globulins, are preserved in a native form, said precipitates mixed and resolved in a chemically and physiologically adapted solvent, said solvent eventually containing also supernatants of the fractionation steps, (c) adjustment of the mixture to a content of 50–70% albumin and 30–50% globulin, related to the entire protein content, (d) stabilizing, purification and drawing off the preparation in a suitable manner.

4 Claims, 1 Drawing Figure

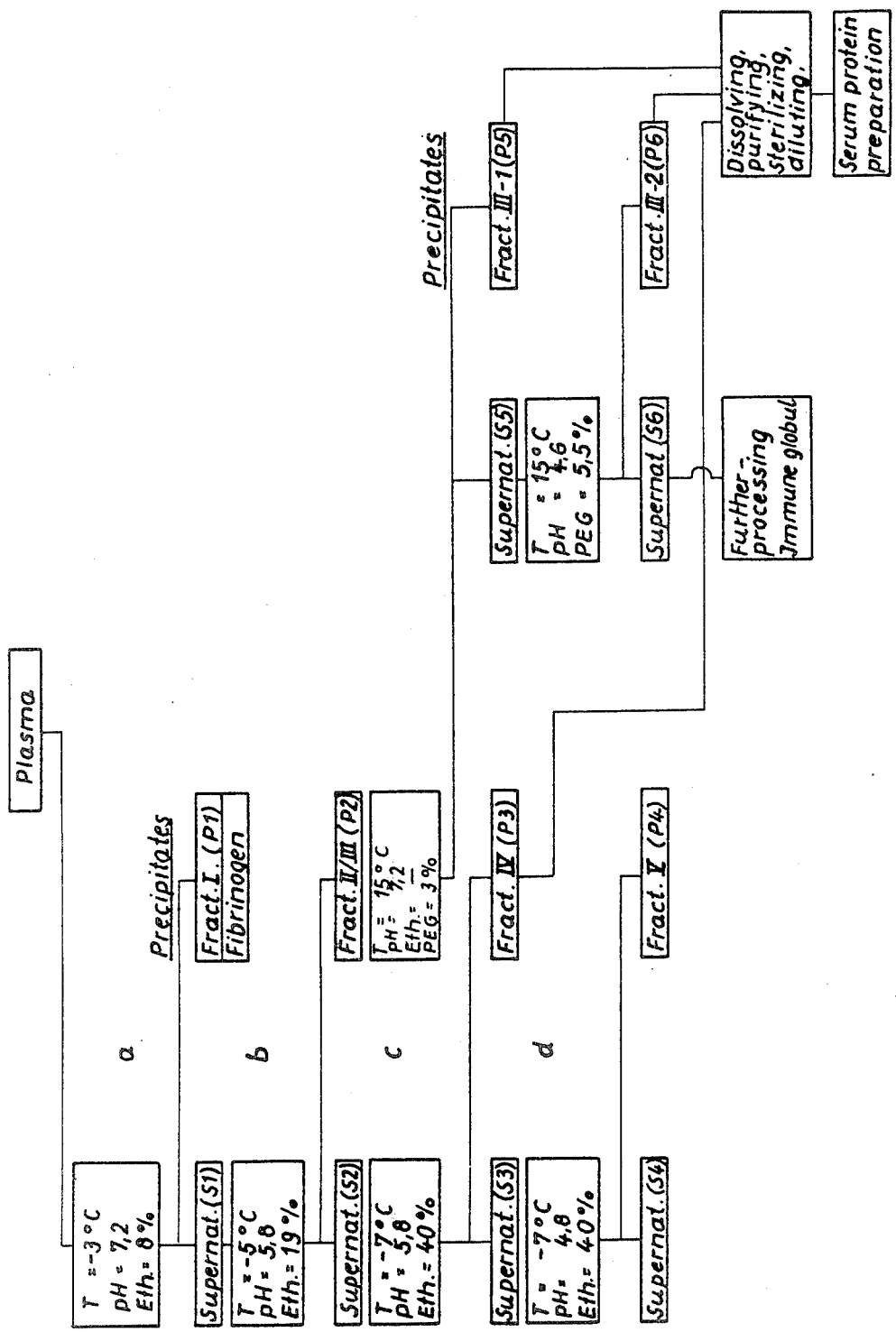

PROCESS OF PREPARING A SERUM PROTEIN COMPOSITION FOR INTRAVENOUS APPLICATION

The present invention relates to a process of preparing a serum protein composition for intravenous application or administration, in which process, starting from a human blood protein solution, a stabilized, universally applicable preparation or composition is prepared which contains dissolved in an aqueous isotonic solution, such proteins in which the ratio of globulins and albumins corresponds substantially to that of the native blood serum.

Serum protein preparations or compositions represent valuable blood derivatives. Tha albumin contained in such compositions functions as a transporting protein. These compositions contain further functional proteins, such as transferrin, ceruloplasmin, $\alpha_1$-antitripsyn and particularly the immune globulins. Of importance are the antibodies which are present in the $\gamma$-globulin. Due to the passive immunization caused by these substances, they are suitable for prophylactic therapy, and they strengthen the body weakened by loss of blood.

A serum protein composition which should be suitable to be intravenously administered to a human patient has to comply with two strict requirements:

(1) The composition must form a storable product;
(2) infection carriers (viruses or bacteria) should be neutralized reliably. This applies particularly to the carrier of virus hepatitis.

Serum protein compositions are normally provided in the form of an aqueous solution of the stable proteins having an electrolyte content that is tolerable to the body. The total protein content is normally 5 percent by weight (i.e. 5,000 milligrams per 100 milliliters).

The literature shows to be known a process for the preparation of a serum protein composition suitable for intravenous application or administration, which composition is obtained directly from human blood in a number of process steps (W. Stephan, "Hepatitis-Free and Stable Human Serum for Intravenous Therapy"; XXIVth Sc. Meeting of the Blood Research Institute, Vox Sanguin, V. 20, (p. 422–457)).

The conventional process is performed in the following steps:

(a) Recovery of a natural serum from donor blood upon removal of the solid constituents (blood corpuscles, blood platelets) and recovery of a serum having a protein concentration of about 7.5% and a pH of from 7.2 to 7.8.

(b) For the removal of the lipoproteins which can be easily denaturalized, 2.0 g of Aerosil 2491/380 (Aerosil: registered trademark of the firm Degussa, for a colloidal silicic acid) are added per 100 ml of serum. The suspension is agitated for 4 hours at 45° C., cooled, and the sediment is removed by centrifuging. The lipoproteins are thereby quantitatively bonded to the Aerosil so as to be removed from the blood serum.

(c) Filtering of the solution through a microfilter for the removal of any suspended particles still present in the solution.

(d) For sterilization, the solution is mixed with 0.3 g $\beta$-propiolactone per 100 ml of solution at a temperature of 5° C. (pH 8.0) and irradiated with ultraviolet light.

The thus obtained serum has the following composition (based upon 5,000 milligrams contained in 100 milliliters):

| Substance | Content | Function |
|---|---|---|
| Albumin | 3,060 | Oncotic activity; transport of nutritive materials, vitamins, hormones, medicaments. |
| IgG | 820 | Antibody to viruses and bacteria. |
| IgA | 185 | Antibodies protecting the mucous membrane. |
| IgM | 75 | Antibodies to bacteria and toxines. |
| Prealbumin | 17 | Tyroxine bond. |
| $\alpha_1$-antitrypsin | 162 | Inhibitors to proteolytic enzymes. |
| $\alpha_2$-macroglobulin | 141 | |
| Haptoglobulin | 110 | Bonding and transport of free haemoglobulin. |
| Haemopexin | 75 | Bonding and transport of free haemin. |
| Transferrin | 195 | Transport of $Fe^{++}$ |
| Coeruloplasmin | 14 | Transport of $Cu^{++}$ as peroxidase. |
| Cholinesterase | 3.0 E/ml | Splitting of succinylcholin. |

The above Table also reveals the functions of the various constituents of the serum protein composition.

The composition prepared in accordance with the conventional process is commercially available. This composition may be applied without complication.

However, it is considered to be disadvantageous with respect to the preparation and application that the composition is very costly because of the high-quality starting material—i.e. human blood—and cannot be made available to a sufficient extent. Add to this that the contents of the particularly highly active antibodies IgG, IgA, IgM is relatively low in correspondence with the presence of these substances in the human blood.

Accordingly, it is the object of the present invention to provide a process for the preparation of a serum protein composition for intravenous administration, in which the starting substances are less expensive and rare. This process should allow to use for the preparation of valuable serum protein compositions such starting substances which have not, or inadequately only, been processed or recovered heretofore. It is a further object of the invention specifically to increase the content of active antibodies or other proteins of the serum without thereby increasing the cost of preparation to any substantial degree.

In the above-mentioned process, this object is solved by using as the starting material, fractions of human blood plasma which are recovered from human serum with the use of one or more fractionating steps serving to enrich (concentrate) or isolate, respectively, individual ones of the blood protein constituents with these latter constituents being substantially preserved in their native form; and characterized by the fact that the fractions of the starting material are provided with a composition of albumins and globulins equivalent to that of the blood serum, by adjustment (standardization) of the mixture, stabilization, purification and concentration or dilution, respectively. Especially, this is performed by the steps of claim 1. The generalized wording of the claim for patent protection states that, although it is started with human blood as the starting material, the preparation of serum protein composition in accordance with the present process is no longer performed directly on the basis of the native serum, but that other intermediate fractionation products are employed which result from the fractionation of blood. In this connection, it is an object of the present invention to employ well-known process products which have not been utilized heretofore, to use uncomplicated process steps, and to increase the recovery of the proportions of useful products present in the human blood.

In particular, the process according to the invention makes use of the fact that the blood fractionation according to COHN yields certain fractions which could heretofore not, or incompletely only, be further processed.

The process according to COHN is based upon the fractionation of the blood plasma with the use of ethanol as a precipitant under precisely determined conditions of temperature, of the pH, of the ion densities and of the ethanol content. The COHN process is described, for instance, in the following publications:

COHN, E. J. et al.: "J.Amer.Chem.Soc." 72 (1950), p. 465-474
COHN, E. J. et al.: "J.Amer.Chem.Soc." 68 (1946), p. 459-475
U.S. Pat. Nos. 2,390,074 and 2,469,193.

The enclosed flow diagram shows the various process steps. In this diagram, the expression "% of ethanol" always refers to percents by volume, measured at 25° C. The starting plasma is obtained from donor blood. 500 milliliters of human blood are each collected in 50 milliliters of a 4% solution of sodium citrate. Initially, the solid constituents of the blood are separated from the plasma; the plasma of a plurality of donors is pooled.

In step a according to the flow diagram, the crude fibrinogen is removed from the plasma by adding thereto cold 53.3% ethanol up to a concentration of 8%. The temperature is maintained at from $-2.5°$ to $-3.0°$ C. The precipitate P 1—fibrinogen—is removed by centrifuging. The supernatant S 1 is further processed.

Step b again comprises the addition of 53.3% ethanol to the supernatant liquid S 1 until a concentration of from 18 to 25% of ethanol in the liquid reached. The temperature is kept at $-5°$ C., and the pH is adjusted to 5.8. The precipitate P 2 is precipitated, which is designated as fraction II/III or as γ-globulin fraction. This precipitate includes the immune globulins and other physiologically significant proteins. The precipitate P 2 is removed by centrifuging at $-5°$ C. The supernatant liquid S 2 is further processed.

Step c involves the further treatment of the supernatant S 2. The ethanol concentration is set to 40%. Similarly as in step b, the temperature and the pH value are set to $-7°$ C. and to 5.8, respectively. By centrifuging, the precipitate P 3, also termed fraction IV, is obtained. The latter contains the α-globulins and β-globulins. The supernatant liquid—Supernatant S 3—is thereafter further processed. To this end, the conditions of temperature ($-7°$ C., pH=4.8) and ethanol concentration=40% are maintained. In this way, precipitate P 4 is precipitated, namely to the so-called crude albumin, which is purified and sterilized in a manner known per se. The supernatant liquid—Supernatant S 4—is disposed of.

The γ-globulin fraction II/III is further processed by the following steps:

Precipitate P 2 is suspended in a citrate-phosphate buffer at a pH of from 7.0 to 7.4. The temperature is held at 15° C. 3% of polyethylene glycol (PEG) 4,000 or 2.5% of PEG 6,000 are added.

The PEG used in practice comprises a mixture of nonvolatile polyethylene glycols which are soluble both in water and in organic liquids and which have a molecular weight on the order of from 4,000 to 20,000. A mixture of polyethylene glycols of this type having an average weight of 4,000 is termed PEG 4,000.

Upon thorough agitation and after a reaction period of from ½ to 4 hours, the mixture is centrifuged, whereby Supernatant S 5 and fraction III-1 (precipitate P 5) are formed. Supernatant S 5 is again treated under modified conditions (pH 4.6; PEG 4,000 up to about 5.5%; temperature=15° C.) and fractionated. Fraction III-2 (precipitate P 6) and Supernatant S 6 are formed, the latter containing primarily the immune globulin IgG. The globulins of fractions III-1 and III-2 are enriched or concentrated to substantial degree with the immune globulins IgG, IgA and IgM. Further, $\alpha_1$-antitripsin, $\alpha_2$-haptoglobulin, coeruloplasmin, transferrin and haemopexin are present in concentrated form.

In general, fractions III-1 and III-2 are not further processed. These fractions are available in large quantities, because it is in the first line the albumin that is recovered from the blood, while the γ-globulins play a secondary role only.

As the starting products for the process according to the invention, mainly fraction IV as well as fractions III-1 and III-2 of the above-described fractionation are employed (precipitates P 3, P5, P 6).

These fractions are mixed in predetermined rations by adjusting the ratio to from 50 to 70% of albumin of from 50 to 30% of globulins, respectively, based on the total protein. It is possible in this way to select in the above-mentioned ratio the same values as are present in the native serum proteins, too.

However, by correspondingly increasing the additions of the globulin portion or of the proportions of fractions III-1 and III-2, it is also possible to specifically increase the proportion of globulins in the form of IgM and IgA.

In a preferred mode of operation, it is contemplated that fractions IV, III-1 and III-2 (sediments) are suspended in a normal saline solution or in a suitable buffer solution, respectively, in the following quantities:

Fraction IV from 30 to 80 percent by weight
Fraction III-1 from 0 to 70 percent by weight
Fraction III-2 from 0 to 70 percent by weight.

based upon a total protein content corresponding to 100% each. More especially, the fractions may be suspended in the solution in the following quantities:

Fraction IV 40 to 60 percent by weight
Fraction III-1 20 to 30 percent by weight
Fraction III-2 20 to 30 percent by weight.

Likewise, it is possible to recover the serum protein compound from fractions III-1, III-2 or IV only, and to prepare these fractions from separate fractions in a stable, dissolved form as the preparation or composition, for the concentration of specific plasma proteins. Similarly, desired ratios of components may be produced from fractions III-1, III-2 and from fraction IV.

The substances mixed in a fixed ratio and suspended in a suitable buffer or saline solution are subjected to a pre-purification, In such pre-purification, the lipid factors of the α- and β-globulin series are removed by adsorption to suitable adsorbents (Aerosil, bentonite or other silicic acid containing complex compounds).

Thereupon, the product is purified by filtering and dialyzed, and the solution is concentrated. Normally, a separate sterilizing step is not necessary. However, such sterilization may be performed in the well-known manner. For example, two methods are used for eliminating viruses:

(a) Pasteurizing by heating to 60° C. for 10 hours. This method suffers from the drawback that numerous serum proteins are denatured under the above conditions.

(b) Combination of β-propiolactone treatment and ultraviolet irradiation (method according to Lo Grippo; Fed. Proceedings 15, page 518, 1959). This method allows to sterilize sera and plasmas under mild conditions; the storage stability is not improved thereby, however.

In general, in accordance with the present process the mixture of the starting components, after having been adjusted or standardized to a specific protein content and to a specific ratio of the proteins, is subjected to a similar process as is conventional for the serum (W. Stephan, loc. cit.). Surprisingly, it is in this way possible to prepare a serum protein composition which is superior to the conventional composition in its effectiveness or activity, due to its increased content of immune globulins IgM or IgA, respectively.

Of course, it is feasible to remove from the individual fractions as such the constituents tending to become denatured and thereafter to mix, concentrate and stabilize the purified fractions. Also, it is feasible to use as the starting material a fractionation product from a fraction with rivanol. To its end, fractions II, III and IV according to STEINBUCH are suitable, which fractions are described in Vox Sanguin. (V. 23, pages 92 to 106).

Preferably, operating with adsorbents is effected in a concentration of from 200 to 500 milligrams of silicic acid per gram of total protein and at a temperature of up to 50° C. The substances are intimately mixed, whereupon the adsorbent loaded with the lipoproteins is separated.

As experiments have shown, the most favorable results are obtained at temperatures of between 20° and 50° C. or at pH values of between 6.5 and 8, respectively.

The following examples serve to explain the process in greater detail.

EXAMPLE 1

To 300 liters of normal saline solution (aqua destillata containing 1.7 percent by weight of NaCl, adjusted to a pH of 4.6 by using 0,2 n of HCL)—termed solvent in the following—, 10 kp of COHN fraction IV showing the following analysis of the protein constituents, are added and suspended therein:

55% of albumin
10% of $\alpha_1$-globulin
8% of $\alpha_2$-globulin
15% of $\beta$-globulin
12% of $\gamma$-globulin Fraction IV contains about 50% of solids (protein, salts) and 50% of residual moisture (H$_2$O; residual ethanol).

Further, 5 kp (kiloponds) of COHN fraction III-1 (subfraction) are added, which fraction shows the following analysis of the solid constituents (percent by weight):

15% of albumin
2% of $\alpha_1$-globulins
13% of $\alpha_2$-globulins
17% of $\beta$-globulins
53% of $\gamma$-globulins, and 5 kp of COHN subfraction III-2 are suspended therein, which subfraction has the following composition:

8% of albumin
3% of $\alpha_1$-globulins
9% of $\alpha_2$-globulins
25% of $\beta$-globulins
55% of $\gamma$-globulins.

The ration between solids and residual moisture is substantially identical in all of these fractions.

The 20 kp pf "moist" fractions are suspended and stirred in the solvent. Hereby, the pH is maintained at a constant value of 4.6. Soluble substances present in the fractions are dissolved or suspended in the solvent. Coexisting, insoluble components cause turbidity. The insoluble substances comprise a portion of 12 percent by weight, based on the total content of solid substances. The insoluble substances involve particularly denatured globulins, including lipoproteins which are not required in the further course of the process. These latter substances are therefore removed in a centrifuging step.

The supernatant liquid is slightly turbid and of yellowish color.

By adding 0.2 n of NaOH, the pH is adjusted to 7.4. Pure colloidal silicic acid is added to the solution until a concentration of 5 percent by weight is reached, and this silicic acid is admixed by stirring. The liquid is heated to 45° C. (about 1° C. per minute), while keeping the pH constant. When the final temperature of 45° C. is reached, the liquid is agitated for 4 hours. During this process step, the storage instable proteins are bonded to the silicic acid to form a precipitate which is removed by centrifuging.

The supernatant liquid from the centrifuging step is subjected to a clarifying filtration over active carbon filters (manufactured by the firm Seitz (AKS-Filter)). The thus obtained filtrate is a clear liquid of amber color. The liquid is concentrated to about 25% of the initial volume by means of a dialysis concentration method (Millipore cassette system, pore size of the membrane or diaphragm 10,000 Daltons). Following this step, the solution has a total protein concentration of from about 3.4 to 4.5 percent by weight.

An analysis shows that substantially all of the blood constituents having a molecular weight of less than 10,000 have been removed from the concentrate by the dialysis concentration step. These constituents include particularly those substances which are undesirable in a protein, e.g. the oligo peptides showing a vaso-active effectiveness.

Following this, the concentrate is subjected to a dialysis with three times the volume of a 9 percent weight NaCl solution for the final removal of the above-mentioned "impurities" and for the adjustment of the electrolyte. The dialysis is performed in the same devices and with the same diaphragms as have been employed in the concentration step.

This processing is followed by another concentration step at the termination of which step a total concentration of the protein of from 6 to 10% is present. Then, the physiological conditions of the isotonic parameters according to the human blood are standardized by means of a NaCl solution, and the total protein concentration is set to 5 percent by weight.

The analysis of the protein recovered according to example 1 shows the following values:

| (based on 100 milliliters and a Protein content of 5,000 milligrams) | |
| --- | --- |
| Albumin | 2,925 milligrams |
| IgG | 1,500 milligrams |
| IgA | 380 milligrams |
| IgM | 285 milligrams |

The thus standardized solution is additionally filtered for clarification through a germicidal filter (EKS II; Seitz, Kreuznach). The sterile filtration is performed with the aid of membrane filters.

In its finally bottled state, the composition is now ready for intravenous administration.

EXAMPLE 2

In the same manner as in example 1, the following materials are dissolved in 300 liters of solvent:

7,5 kp of COHN fraction IV
4 kp of COHN fraction III-1
and 8,5 kp of COHN fraction III-2.

The composition of these fractions is identical to that of example 1. The fractions are mixed by stirring with the solvent, and the pH is maintained at 4.6.

60 grams of Aerosil 2491/380 per liter of solution are added to the latter, and the pH is brought to 7.6. The mixture is agitated for 4 hours at 47° C. and thereafter cooled to 18° C. and subjected to alluvial filtration. This filtration step is performed in an upright alluvial or precoat filter, type CHF-S of the firm Schenk, Filterbau, Schwäb. Gmünd. As the filtering aid, Hyflo Super Cel is employed in a concentration of 8 percent by weight, based upon the filter volume. Likewise, kieselguhr Celite 545 in a concentration of 5% may be used as the filtering aid.

EXAMPLE 3

Following the purification, the various solutions are combined and subjected to a dialysis concentration method equivalent to that of example 1. However, the solutions, if desired, may be processed into the final concentrate in the manner explained in example 1, whereupon these solutions may be selectively used individually or combined in any desired manner.

EXAMPLE 4

10 kp of fraction III-1 and 10 kp of fraction III-2 are dissolved in 200 liters of a phosphate-citrate buffer solution (0.066 moles of phosphate-citrate), within a period of about 3 hours. The pH is set to 7.50, and after a further dilution to 300 liters by using the above-mentioned buffer solution and with the addition of 100 grams/liter of Aerosil/bentonite (2:1), the solution is stirred or agitated for 4 hours at 45° C. After cooling to 10° C., the suspension is bright filtered on an alluvial or precoat filter precoated with 1.0 kg of kieselguhrcelite 545 per square meter of filter area with a filter performance of 50 liters/square meter hour. This is followed by purification filtration (using a Seitz-AKS4 filter) and by dialysis concentration as explained in examples 1 to 3. The final concentration of the solution ready for use is set to 5% of protein. This provides the following average composition:

| (Protein | 5,000 milligrams) |
| --- | --- |
| albumin | about 1,800 to 2,000 milligrams |
| globulins | 3,000 to 3,200 milligrams |
| IgG | about 1,450 milligrams |
| IgA | about 750 milligrams |
| IgM | about 500 milligrams |

EXAMPLE 5

Instead of a fractionated precipitation, the COHN fractions I to III and IV-1 may be precipitated in a single step at a concentration of 40% of ethanol and a pH of 5.8. Fraction IV-1 means a subfraction of fraction IV (compare e.g. U.S. Pat. No. 2,710,293). The precipitate is isolated. 20 kp of the precipitate are suspended in 300 liters of solvent according to example 1 and further processed in the manner described in example 1.

EXAMPLE 6

It is known to effect a fractionated precipitation of the human plasma with Rivanol (2-ethoxy-6,9diaminoacidinilacetate) (STEINBUCH, Vox Sanguin. 23, p. 92 to 106). In accordance with the processes described in the latter publication, precipitates II, III and IV are obtained. These precipitates may be processed to yield the serum protein composition according to the invention, too. 10 kp of precipitates II, III and IV each, a total of 30 kp, are suspended in 300 liters of the solvent according to example 1 and processed in accordance with the processed in accordance with the process explained in example 1.

I claim:

1. A process for preparing a stable serum protein composition of improved passive immunilogical properties, suitable for use in prophylactic therapy and the strengthening of the human body weakened by loss of blood, wherein the starting product for said process is more readily available than the human blood which is used in conventional processes for obtaining serum protein compositions, said process comprising the steps of:
   (a) mixing and suspending plasma fractions together in a suitable physiologically acceptable solvent to produce a mixture, said fractions and the amounts thereof being selected in such a manner that an immunologically effective amount of active antibodies is incorporated into the mixture, said fractions being characterized as equivalent to:
      (i) COHN-fractions IV and II/III, or
      (ii) fractions II, III and IV according to Steinbuck;
   (b) removing the insoluble components remaining in the mixture and recovering the supernatant;
   (c) stabilizing and purifying the super natant by removing storage instable proteins, thereafter subjecting the supernatant to a clarifying filtration and concentrating the resulting solution to remove substantially all blood constituents having a molecular weight of less than 10,000 to produce a purified solution;
   (d) standardizing the purified solution to the physiological conditions of the isotonic parameters according to human blood by means of a NaCl solution.

2. A process according to claim 1, wherein said fractions COHN-fractions are selected from the group consisting of fractions IV, III-1 and III-2.

3. A process according to claim 2, wherein said mixture comprises the following proportions of fractions:
Fraction IV 30 to 80 percent by weight
Fraction III-1 0 to 70 percent by weight
Fraction III-2 0 to 70 percent by weight.

4. A process according to claim 3, wherein said mixture comprises the following proportions of fractions:
Fraction IV 40 to 60 percent by weight
Fraction III-1 20 to 30 percent by weight
Fraction III-2 20 to 30 percent by weight.

* * * * *